Figure 1:
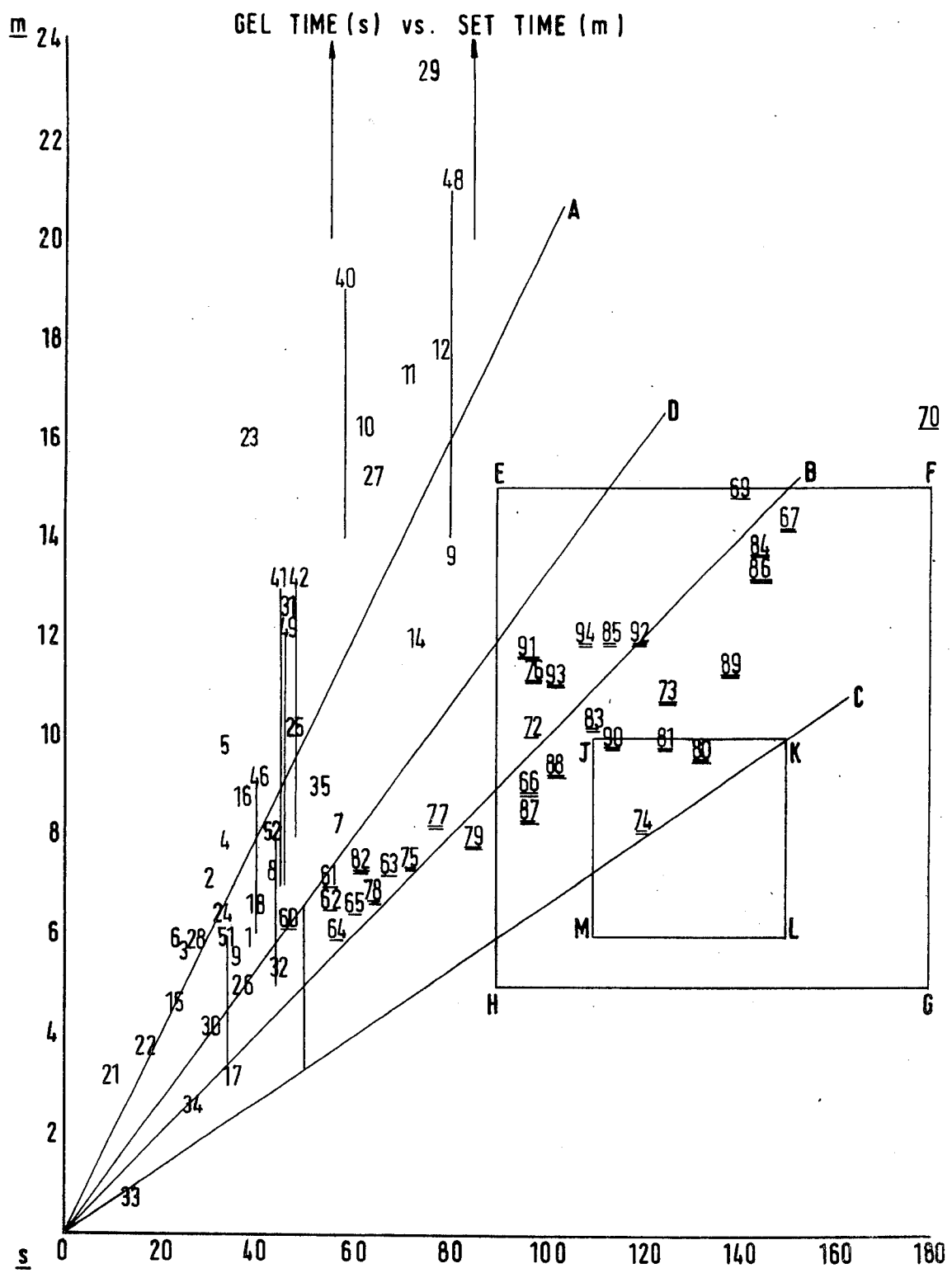

United States Patent [19]

Potter et al.

[11] 4,123,416

[45] Oct. 31, 1978

[54] CURABLE COMPOSITION COMPRISING A CALCIUM FLUORO-ALUMINO SILICATE GLASS AND POLY(CARBOXYLIC ACID) OR PRECURSOR THEREOF

[75] Inventors: William D. Potter, Ware; Andrew C. Barclay, Harlow; Reginald Dunning, Near Wigan; Richard J. Parry, Southport, all of England

[73] Assignee: Smith & Nephew Research Limited, Esses, England

[21] Appl. No.: 685,486

[22] Filed: May 11, 1976

[30] Foreign Application Priority Data

May 13, 1975 [GB] United Kingdom ............... 20196/75
May 13, 1975 [GB] United Kingdom ............... 20197/75
Aug. 15, 1975 [GB] United Kingdom ............... 34128/75

[51] Int. Cl.$^2$ ............................................. C08K 7/14
[52] U.S. Cl. ................................... 260/42.18; 32/15; 106/35; 106/52; 128/87 R; 260/42; 526/317
[58] Field of Search ............ 106/52, 35; 260/42.18, 260/42; 128/87 R; 526/317; 32/15

[56] References Cited

U.S. PATENT DOCUMENTS 1,529,259  3/1925  Locke et al. ...................... 106/52
3,814,717  6/1974  Wilson et al. ..................... 106/35
3,981,736  9/1976  Broemer et al. .................. 106/52

FOREIGN PATENT DOCUMENTS 2,252,837  6/1975  France.
1,316,129  5/1973  United Kingdom.

OTHER PUBLICATIONS

Kirk-Othmer, Encyclopedia of Chemical Technology (2nd ed.), (Interscience) (N.Y.) (1966), p. 580, (vol. 9).

*Primary Examiner*—Melvyn I. Marquis
*Attorney, Agent, or Firm*—Burgess, Dinklage & Sprung

[57] ABSTRACT

A novel calcium fluoroaluminosilicate glass consisting essentially of from 25 to 35% by weight of silicon calculated as silica, from 30 to 40% by weight of aluminum calculated as alumina, from 20 to 35% by weight calcium, calculated as calcium oxide, and up to 9% by weight fluorine (preferably 4-7%) can be associated with a poly(carboxylic acid) e.g. as an intimate mixture of glass and acid to constitute a composition curable on contact with water and useful, for example, as a loading on a splinting bandage. Such a bandage preferably has a ratio of set time to gel time from 4:1 to 8:1 with a minimum gel time of 60 seconds.

35 Claims, 5 Drawing Figures

CURABLE COMPOSITION COMPRISING A CALCIUM FLUORO-ALUMINO SILICATE GLASS AND POLY(CARBOXYLIC ACID) OR PRECURSOR THEREOF

This invention relates to curable compositions, usually of the type wherein addition of water to a dry mixture of components leads to curing, but including the type wherein an aqueous solution of one component is added to the other component in powder form. The curable compositions of the invention have as one component a powdered ionleachable fluoroaluminosilicate glass and as the other a poly(carboxylic acid) or precursor thereof, whereby ions leached from the glass in the aqueous environment lead to cross-linking of the polymer to form a polycarboxylate cement.

The invention primarily relates to splinting bandages or like sheets of material wherein a mixture of the powdered glass and the polymer particles supported on and/or intermingled with a fibrous substrate is cured after contact with water into a rigid support member for part of the body. Making such bandages, applying them to the limb, and the bandage in hardened and set form are all aspects of the invention under this heading.

The invention however also relates to dental or like surgical cements based on the above materials, either as a two-component dry particulate mixture to which water is added or as a two-part package containing the powdered glass in one part and an aqueous solution of acid in a suitable amount and concentration in the other, for mixing prior to use.

The selected glass powder used in the above aspects of the invention, and its method of manufacture, also form part of the present invention.

Polycarboxylate dental and like surgical cements are described for example in British Patent No. 1,316,129. The disclosure of this patent is predominantly directed towards two types of relatively high fluorine-content powdered fluoroaluminosilicate glass to which are added specific amounts of specific solutions of poly(carboxylic acids). This sets to form a dental cement, useful for filling or lining the cavities in teeth or a surgical cement presumably envisaged for attaching together broken bones or for attaching prostheses to bones. The possibility of making such cements from a two-component dry mixture of the powdered glass and powdered poly(carboxylic acid), by adding to this a specific amount of water, is briefly mentioned in the said British patent but no details of procedure are given.

French Patent Specification No. 2,252,837 is based on the discovery that such a two-component dry mixture as briefly mentioned in British Patent No. 1,316,129, and by extension other two-part dry mixtures, e.g. of metal oxides and poly(carboxylic acid) turn out to be suitable for use on a splinting bandage.

A splinting bandage is a web of fibrous fabric material supported on which, and/or intermingled with the fibres of which, is a waterhardenable particulate material. Conventionally the material has been plaster-of-paris (POP) which is essentially calcium sulphate hemihydrate $(CaSO_4)_2H_2O$ Such a bandage is dipped into water and wrapped while still wet around a part of the body to be restrained or supported, for instance a broken arm. This wet bandage can be manipulated and smoothed into a desired shape until it gels. This takes normally from 1½ to 4 minutes with a POP bandage. However, the bandage at this stage is still not hard enough for the patient to be left unattended, and typically is takes about 5 to 15 minutes for the bandage to harden or set sufficiently.

There are different grades of POP leading to bandages of somewhat different characteristics. The technician in this field is thus well aware of the desirability of using a bandage which is cheap enough for bulk use; has a low exotherm, i.e. does not become uncomfortably hot as it hydrates and gels; gives a set cast of good tensile and flexural strength; does not delaminate; gels and sets in a convenient time; and is not prone to shrinkage on drying.

According to the French Patent Specification above it has been discovered that the two-part mixture of powdered materials hitherto only briefly mentioned as a dental cement can be used in a bandage instead of the essentially one-component POP bandage. This is surprising in view of the facts that it has unknown exotherm, flexural stress and delamination characteristics; has a different gel/set time for that desirable for bandages; and has only hitherto been selected for use in a wet environment, where shrinkage is impossible. Moreover, it was proposed as (and important in) a dental cement to use the two-component mixture only with a specific amount of water, to give a doughy material suitable for insertion into a downwardly opening cavity if necessary whereas, as a splint, the loaded bandage is immersed in gross excess of water to give a wet fluid paste. However, having tried this material the Applicants in respect of the above French Patent Specification surprisingly found not only that it functioned to fulfil the above desiderata but also that it gave a cast of good strength/weight ratio and hence low weight (thereby saving expense over what might have been anticipated having regard to the cost of the raw materials used) which was water-resistant and X-ray-transparent.

Two-part compositions within the range given in the above-identified French Patent Specification work in the sense that they give splinting materials which gel and set. Some of them e.g. of the zinc oxide/poly(acrylic acid) type gel very quickly and are thus best utilised for building up casts from individually short lengths of bandage, with minimum application and manipulation time for each. Others e.g. some of the fluoroaluminosilicate glass compositions take a long time to set (25–30 minutes or more) and are therefore best used where the site of the cast and/or the whole patient can be conveniently immobilised for this length of time.

The present invention is based upon the realization that any such departures from the conventional gel and set times of POP bandages need either operator-retraining or physical reorganisation of the casualty/orthopaedic units or both. Splinting bandages need in practical terms therefore (i) to possess more or less conventional gel and set times (ii) to be reproducible in such characteristics from one batch to the next and (iii) to be tolerant of individual operator differences in dipping and wrapping times and procedures without departing from their desired characteristics.

Surprisingly, the Applicants have found that by using a powdered fluoroaluminosilicate glass/powdered poly/carboxylic acid) type of system wherein the fluorine content of the glass is held at a low level and most preferably within a narrow range these desiderata of timing, reproducibility and tolerance can be achieved.

In one aspect therefore the present invention provides a calcium fluoroaluminosilicate glass consisting essentially of from 25 to 35% by weight of silicon calculated as silica, from 30 to 40% by weight of aluminum calculated as alumina, from 20 to 35% by weight calcium, calculated as calcium oxide, and up to 9% by weight fluorine.

In this Specification and claims the contents of elements other than fluorine are expressed as if the elememts were present as their oxides, and the fluorine content is expressed as if present as free fluorine, the total content of fluorine plus the oxides of the elements adding up to 100%.

Preferably the fluorine content is below 7% by weight, and especially from 4% to 7% by weight with from 4.5% to 6.0% being a further preferred range. The silica:alumina ratio must lie between 0.625:1 and 1.167:1, preferably it lies between 0.7:1 and 1:1, and most preferably between 0.7:1 and 0.8:1. By "consisting essentially of" we mean that the glass can contain other constituents provided that these do not detract from the desirable properties of the glass (provided by the essential constituents) to an unacceptable extent; generally the glass may contain up to about 10% by weight of normally encountered compatible glassmaking ingredients, for example sodium oxide and boric oxide, preferably with no one ingredient being over a level of about 5% by weight.

A preferred glass comprises, in weight percentages calculated as before, $SiO_2$ 25% to 35%, $Al_2O_3$ 30% to 38%, CaO 23% to 35%, and $F_2$ 4% to 7%.

The low silica:alumina glasses are intrinsically unusual glasses, and it is novel to compound them with a low level of fluorine.

As explained in detail below, they have utility when powdered as components in poly(carboxylic acid) waterhardenable compositions, giving valuable properties in respect of gel and set times for such compositions.

It is particularly valuable if the glass is clear and homogeneous rather than opaline or translucent. Opaline powdered glasses have been proposed for dental cements because of their appearance. We have found however that the heterogeneities in the glass have a different composition and hardness from the rest of the glass whereby on grinding they adopt a different particle size and, if sieved out, provide a different assay for the resulting powder compared to the original glass. For the low content and narrow ranges of fluorine in the glasses of the invention this can be detrimental. Also, opaline glasses can differ among themselves as to the degree of opalinity and heterogeneities, rendering it difficult to reproduce a given assay from one batch to the next.

The glasses according to the invention may be made by melting a batch comprising 25% to 35% by weight of silica; 30% to 4% by weight, calculated as alumina, of alumina or a precursor thereof; 15% to 30% by weight, calculated as calcium oxide, of calcium oxide or a precursor thereof; and a fluroine-containing compound in an amount to provide up to 9% and preferably 4% to 6% by weight of fluorine in the glass formed; the total calcium content, calculated as calcium oxide being from 20% to 35% by weight; all the weight percentages being based on the total weight of metals in the batch, calculated as their oxide, plus the weight of fluorine in the batch.

The temperature required to achieve melting will depend on the particular constituents used, and their properties; in general, temperature of 1350° C. upwards, conveniently 1400° to 1600° C. are desirable to achieve satisfactory melting to give clear glasses, although, in some cases, lower temperatures may be used. Temperatures in the range 1400° C. to 1600° C. tend to give clear rather than opaline glasses particularly if the glasses are cooled quickly.

On melting the batch there is a loss of fluorine which, we have found in practice, generally amounts to 15% to 20% of the fluorine initially present. Thus it is generally necessary to start with more fluorine in the batch than would theoretically be required to obtain the desired product. For example, to obtain a product containing from 4% to 6% by weight of fluorine it is generally necessary to use sufficient fluorine-containing compound to provide, assuming no fluorine loss, a glass containing from 5% to 7% by weight of fluorine.

An advantage of the low fluorine content of the glass according to the invention is that there is not such a high loss on fusion as with high-fluorine glass. Thus corrosion of the equipment, pollution of the environment, and any possible health hazard to the operative are minimised.

The silica in the mixture can be supplied as such, e.g. as silica sand. The alumina may be present as such or added as a precursor e.g. aluminum hydroxide. Calcium oxide could be added as calcium hydroxide or carbonate.

The fluorine is usually but not necessarily supplied as calcium fluoride or aluminum fluoride, or a mixture thereof. The composition may also contain small proportions of other components, for example components known to be useful as fluxing materials e.g. sodium hydroxide or carbonate yielding sodium oxide in the glass, boric acid yielding boric oxide in the glass, or borax yielding both sodium oxide and boric oxide in the glass.

We have found that certain preferred batches melt readily to give a good glass with little or no tendency for devitrification to occur. The advantages of using a readily melting glass composition which is not prone to devitrification are that it is easier to obtain a homogeneous product than when a less readily melting composition is used, and secondly, since the product is clear and homogeneous, its production can be monitored by optical techniques.

The fluoroaluminosilicate glasses of the present invention, formed from the preferred batches comprise in weight percentages:
$SiO_2$ 25% to 30%
$Al_2O_3$ 31% to 38%
CaO 27% to 33%
F 4% to 7%

Particularly preferred glasses have a calcium oxide (CaO) to silica ($SiO_2$) ratio of at least 1, assuming that all the calcium is present as CaO and all the silicon is present as $SiO_2$.

A second aspect of the invention is the glass as described above in particulate form, preferably with a particle size of less than 100 microns and most preferably with a particle size of less than 50 microns. This can be achieved by pestle-and-mortar grinding or by ball-milling, with sieving if and as necessary afterwards.

A third aspect of the present invention constituted by a curable composition comprising a particulate glass as described above together with a poly(carboxylic acid) or a polymeric precursor thereof such as a poly(carboxylic acid anhydride).

These polymeric materials are usually based on unsaturated monocarboxylic acids, or their anhydrides and unsaturated dicarboxylic acids and their anhydrides, being homopolymers of any one of those, copolymers between any two or more of these or copolymers between one or more of these and one or more further ethylenically unsaturated monomers. Specific compounds are acrylic, itaconic, mesaconic, citraconic, or maleic acid, or anydrides thereof.

Preferred homopolymers are acrylic acid or acrylic acid anhydride homopolymers. Copolymers with acids preferably utilise acrylic acid with acrylamide or acrylonitrile as the ethylenically unsaturated comonomer, or maleic acid with vinyl methyl ether. Copolymers with anhydrides preferably use ethylene, propylene, butene or styrene for this purpose as the ethylenically unsaturated comonomer, e.g. maleic anhydride/ethylene copolymer.

The molecular weight of the polymeric material may be from 1,000 to 1,000,000, values of 50,000 to 500,000 being preferred.

The curable composition may be formulated in different ways. To dispose first of the minor ways, the present invention envisages a two-part package of (a) particulate glass and (b) the polymeric acid preferably in the form of an aqueous solution, or anhydride. There is also the possibility of providing the acid or anhydride as dry powdered material separate from the particulate glass, for activation by adding water. Both of these possibilities find utility in the field of dental and surgical cements.

However, it is a major aspect of the invention to provide the curable composition as a mixture of the particulate glass and particulate polymeric acid or anhydride. The weight ratio (glass:polymer) is suitably from 0.5:1 to 5:1, preferably from 1.5:1 to 4.5:1 and most preferably about 3:1. The polymer preferably has a particle size below 100 microns.

When water is added to such a composition it will first gel and thereafter set. Preferred gel times are from 90 to 180 seconds, although times down to 60 seconds or less and up to say 300 seconds or more can still be utilised. Gel times of from 110 to 150 seconds are particularly preferred since these resemble the working times with plaster-of-paris bandages as described below. Set times of 5 to 15 minutes are preferable although it is possible to use set times of 20 minutes or more in some cases, while shorter set times are obviously no disadvantage.

The ratio between set time and gel time preferably lies between 4:1 and 8:1, with a lower limit of 60 seconds on gel time. This type of ratio, centering on 6:1 is not given by any prior proposed substitute for plaster-of-paris wherein generally speaking acceptable gel times necessitate unacceptable set times and vice versa, the set:gel ratio centering around 12:1.

The gel and set times may be varied to some extent, as discussed below in more detail, by varying the amount of water used to cure the mixture, although we have found that varying the amount from e.g. 40% to 67% still provides useful gel and set times in this system.

Another way of varying the gel and set times is to add an organic dicarboxylic (or higher polycarboxylic acid) or hydroxycarboxylic acid to the composition, e.g. mixed into the glass/polymer particulate mixture as a third particulate component. This appears to exert a chelating effect on the calcium ions produced when water is added, although the exact mechanism is obscure and the effect of adding such acid is not linear on gel and set times. The amounts preferred are from 5 to 15% by weight (based on polymer) and useful acids are tartaric, succinic, oxalic, citric, ascorbic, gluconic or adipic acids, tartaric acid being exemplified below as typical of such acids since it has a useful moderate degree of activity.

It is moreover possible to add to the mixture of particles further particulate materials purely as fillers. Silica and calcined alumina constitute preferred fillers, the gel and set times increasing with increase of filler content.

Another category of additive to the mixture is a particulate watersoluble inorganic crystalline material, e.g. a salt of an alkaline or alkaline earth metal and a strong acid, preferably hydrochloric acid. Monovalent rather than divalent metals are preferable and for cheapness sodium or potassium chloride is preferred. The amount of such material is preferably from 2.5 to 10.0% by weight e.g. about 5% based on the glass and polymer content. The effect is possibly physical rather than chemical, crystals of the salt precipitating within the structure as the water is lost and thereby preventing or minimising shrinkage. However, we have noted that magnesium or calcium sulphates, for example, do not work as well as NaCl, and an alternative hypothesis may be that increased ionic strength of solvent leads to a lower water content in the gel which therefore shrinks less as it eventually sets.

All of the above particulate mixtures can be presented for use in association with a substrate in the form of a flexible carrier which is porous or otherwise provided with interstices.

The mixture is usually an intimate mixture of the two or more types of particle. It may be located at the surface of the flexible carrier, or within the pores or interstices, or both.

A major aspect of the invention is constituted by a splinting bandage wherein an intimate particulate mixture of the glass as described above and the polymeric material as described above is carried on and/or intermingled with the fibres of a fibrous bandage substrate.

The total coating weight of such a bandage can be from 200 to 500 g/m$^2$, i.e. of the order of ten times that of the bandage itself.

The fabric of such a bandage is preferably a Leno weave cotton gauze, as conventional in this art. However, other woven or non-woven (stitched or netted) substrates based on multifilamentary or spun yarns comprising synthetic polymers e.g. polyamides, polyolefins and especially polyesters are also envisaged.

Such bandages may be formed by contacting the substrate with a slurry containing the particulate glass and polymer in an anhydrous liquid and allowing this liquid to evaporate. Contacting can be effected by dipping, brushing, spraying or like manipulative steps but is preferably done by spreading. The solids content of the slurry can be greater than 50% by weight. The anhydrous liquid is preferably a volatile organic medium e.g. methylene chloride. Usually an adhesive or binder will be present in the anhydrous medium, being soluble both in the said medium and in water and serving to minimise loss of solids when the eventual bandage is dipped into water prior to use. Up to 5%, e.g. from 2.5 to 5% of binder is preferable (based on solids content of slurry) and hydroxyalkyl cellulose, specifically hydroxypropyl cellulose are valuable for this purpose.

Such bandages are dipped in water applied while wet to the patient, smoothed and manipulated into the desired shape, and allowed to gel and set. Water uptake is usually about 50% of powder loading, although we have found that the system as described above tolerates operator variability in this regard. A method of treating a human patient, or an animal, utilising such a bandage in the above-specified manner constitutes an aspect of the invention, as does the hardened and set bandage.

The invention will be further described with reference to the following Examples expressed in tabular form.

TABLE I
Comparison Test - Ion-leachable glasses

| No. | Code | Gel Time (secs) | Set Time (mins) |
|---|---|---|---|
| 1 | 1.5/20/20C | 38 | 6.0 |
| 2 | 1.3/20/20C | 30 | 7.2 |
| 3 | 1.5/25/20C | 25 | 5.8 |
| 4 | 1.5/15/20C | 33 | 7.9 |
| 5 | 1.5/10/20C | 33 | 9.9 |
| 6 | 1.7/20/20C | 23 | 6.0 |
| 7 | 1.5/20/20CF | 57 | 8.3 |
| 8 | 1.5/20/20AF | 43 | 7.3 |
| 9 | 1.5/20/20B | 81 | 13.6 |
| 10 | 1.3/20/20B | 62 | 16.3 |
| 11 | 1.5/25/20B | 72 | 17.3 |
| 12 | 1.5/15/20B | 78 | 17.8 |
| 13 | 1.5/10/20B | 113 | 37.3 |
| 14 | 1.7/20/20B | 73 | 12.0 |
| 15 | 2.1/20/20C | 23 | 4.7 |
| 16 | 2.9/20/20C | 37 | 8.8 |
| 17 | 1.5/25/20CF | 35 | 3.3 |
| 18 | 1.5/25/20CF + 30% B | 40 | 6.6 |
| 19 | 1.5/25/20CF + 15% B | 35 | 5.6 |
| 20 | 4.0/20/20C | 38 | 27.7 |
| 21 | 2.9/25/20CF | 10 | 3.3 |
| 22 | 4.0/25/20CF | 17 | 3.8 |
| 23 | 2.9/20/20B | 38 | 16.0 |
| 24 | 1.5/22.5/20CF | 33 | 6.4 |
| 25 | 1.5/25/10CF | 48 | 10.2 |
| 26 | 1.5/25/30CF | 37 | 5.0 |
| 27 | 1.5/20/30B | 64 | 15.3 |
| 28 | 0.7/25/20C | 27 | 5.8 |
| 29 | 0.7/25/20B | 75 | 23.4 |
| 30 | 1.5/30/10CF | 30 | 4.2 |
| 31 | 1.5/30/30B | 47 | 12.6 |
| 32 | 1.5/25/20CF | 45 | 5.4 |
| 33 | 1.5/25/20CF + eq. N | 14 | 0.8 |
| 34 | 1.5/25/20CF + 5% N | 27 | 2.6 |
| 35 | 1.5/36/0 | 53 | 9.0 |

Table I lists glass formulations 1 to 35, all of which are comparison formulations outside of the scope of the present invention. The code used to express the glass composition gives first the weight ratio of silica to alumina; then the number of parts (per hundred of total $SiO_2 + Al_2O_3 + 0$ CaO) of calcium oxide; then the nature and content of additional components expressed again in parts per hundred of the $SiO_2 + 0 \, Al_2O_3 + $ CaO mixture. The abbreviations used are as follows:

C - cryolite $Na_3AlF_6$
CF - calcium fluoride $CaF_2$
AF - aluminum fluoride $AlF_3$
B - boric acid
N - sodium oxide (added as sodium carbonate)

Thus, to take No. 7 as an example, this contains 48 parts silica, 32 parts alumina, 20 parts calcium oxide and 20 parts calcium fluoride.

This can be converted into terms of oxides and fluorine content, by the following specimen calculation.

$$20 \, CaF_2 = 10.26 \, Ca^{++} + 9.74 \, F_2$$

Expressed as oxides, this becomes equivalent to $$14.36 \, CaO + 9.74 \, F^-$$

Adding the CaO content to that of the original oxides, this becomes $$48 \, SiO_2 : 32 \, Al_2O_3 : 34.36 \, CaO : 9.74 \, F_2$$

As a percentage, this equals $$38.8 \, SiO_2 : 25.8 \, Al_2O_3 : 27.8 \, CaO : 7.4 \, F_2$$

The other compositions can be similarly converted, bearing in mind that all aluminum, boron, sodium and calcium content must be expressed as oxide. (The compositions given are strictly speaking those of the charge to the furnace rather than those of the eventual glass, but at the low fluoride contents given it has been found by experience that there is a loss of fluorine of about 15%–20%).

These compositions (batch size 500 g.) were fused at 1400° C. for 85 minutes in a sillimanite crucible within a gas-fired furnace operating in an oxidising mode. Immediately after removal the molten glass was cast on a steel table, allowed to cool to a red heat and then quenched in cold water to give a crazed easily broken-up sheet which was then dried, ground in a mechanical pestle and mortar and sieved to below a particle size of 45 microns.

Each type of glass powder was mixed at a ratio of 5:1 by weight with a polyacrylic acid powder prepared by a precipitation polymerization technique in benzene, having an intrinsic viscosity of 0.7, and sieved to a particle size of less than 106 microns. To this mixture was added 11% (based on the polyacrylic acid) of dry powdered tartaric acid. To this total powder mixture was added water in a powder: water ratio of 2:1. Each test batch was as follows:

Glass 2.5 g
Polyacrylic acid 0.5 g
Tartaric acid 0.06 g
Water 1.5 ml.

To determine gel and set times, the water is added at 20° C. to a container containing the dry powder and the resulting homogeneous wet mix is poured into a cylindrical mould of 25.4 mm internal diameter, 2 mm deep, resting on a glass plate all equipment being kept at 20° C. and 65% relative humidity. Some of the wet mix is kept in the container and the formulation is deemed to have gelled when this, when gently manipulated with a spatula, fails to flow from the spatula end, i.e. is deformable but does not flow. The formulation is deemed to have set when a Gilmore "final" needle (of weight 454 g., diameter 1.06 ± 0.05 mm, cylindrical for 4.8 mm from its plane end at right angles to the rod) lowered vertically on the horizontal surface in the mould and allowed to rest thereon for approximately five seconds leaves no perceptible indentation. Thus 'gel time' extends from commencement of mixing until gelling, and 'set time' from commencement of mixing until setting, each being the mean of three readings.

TABLE II
Comparison Test - Zinc oxide

| No. | Composition (grams) | | | | | | Gel Time (s) | Set Time(m) | |
|---|---|---|---|---|---|---|---|---|---|
| | ZnO | Z44 | PAA1 | PAA2 | TA | HPC | | A | B |
| 40 | 0 | 3.0 | 2.0 | 0 | 0.1 | 0 | 58 | 14 | 19 |
| 41 | 0 | 3.0 | 2.0 | 0 | 0 | 0.15 | 48 | 7 | 13 |
| 42 | 0 | 3.0 | 2.0 | 0 | 0.15 | 0.15 | 48 | 8 | 13 |
| 43 | 0 | 3.0 | 0 | 2.0 | 0.1 | 0 | 77 | 35 | 49 |
| 44 | 0 | 3.0 | 0 | 2.0 | 0 | 0.15 | 87 | 28 | 39 |
| 45 | 0 | 3.0 | 0 | 2.0 | 0.15 | 0.15 | 82 | 29 | 40 |
| 46 | 0 | 3.0 | 1.5 | 0 | 0 | 0.14 | 40 | 6 | 9 |
| 47 | 0 | 3.0 | 0 | 1.5 | 0 | 0.14 | 85 | 20 | 25 |
| 48 | 0 | 3.0 | 0 | 1.0 | 0 | 0.12 | 80 | 14 | 21 |
| 49 | 2.0 | 0 | 2.0 | 0 | 0.4 | 0.12 | 45 | 7 | 12 |
| 50 | 2.0 | 0 | 0 | 2.0 | 0.4 | 0.12 | 55 | 20 | 28 |
| 51 | 2.0 | 0 | 2.0 | 0 | 0.4 | 0.15 | 35 | 3 | 6 |

TABLE II-continued

| | Comparison Test - Zinc oxide | | | | | Gel Time | Set Time(m) | |
|---|---|---|---|---|---|---|---|---|
| | Composition (grams) | | | | | | | |
| No. | ZnO | Z44 | PAA1 | PAA2 | TA | HPC | (s) | A | B |
| 52 | 2.0 | 0 | 0 | 2.0 | 0.4 | 0.15 | 45 | 5 | 8 |

Table II lists formulations 40 to 52 all of which are also comparison formulations but based in this case on zinc oxide rather than on ionleachable glass powder.

The abbreviations in the Table have the following meanings:

Z44 - coated zinc oxide produced by 4 g. of palmitic acid with 100 g. of Durham Code 10 zinc oxide (0.22 microns) after 60 min. in methylene chloride solution.

PAA1 - polyacrylic acid as in Table I, polymerized in and precipitated from benzene solution, sieved to below 106 microns particle size.

PAA2 - as PAA1, but prepared in petroleum ether solution.

TA - tartaric acid.

HPC - hydroxypropyl cellulose.

ZnO refers to the uncoated zinc oxide. Set time A was with a 454 g. needle loading as in Table I but Set Time B was with a 1,000 g. needle loading, since these casts have a different pattern of strength build-up from those of Table I. In all cases the powder water ratio was 2:1, as before.

TABLE III

| No. | Code | Gel Time (secs) | Set Time (mins) |
|---|---|---|---|
| 60 | 0.7/25/20CF | 45 | 6.3 |
| 61 | 1.0/25/20CF | 55 | 7.2 |
| 62 | 1.0/30/10CF | 55 | 7.0 |
| 63 | 1.0/30/4½CF | 68 | 7.4 |
| 64 | 1.1/35/7 AF | 56 | 6.1 |
| 65 | 0.9/30/10CF | 60 | 6.7 |
| 66* | 1.0/30/10AF | 98 | 9.1 |

Table III shows formulations 60-66 of glass according to the invention. The procedure was identical to that used in Table I. The asterisk indicates a preferred composition within the 5%-7% equivalent range of fluorine content in the charge, yielding 4%-6% in the glass.

TABLE IV

| | Composition (Wt. %) | | | | | | Gel Time | Set Time |
|---|---|---|---|---|---|---|---|---|
| No. | SiO$_2$ | CaO | Al$_2$O$_3$ | F$_2$ | Na$_2$O | B$_2$O$_3$ | (secs) | (mins) |
| 67 | 31.30 | 26.90 | 36.80 | 5.0 | 0 | 0 | 150 | 14.4 |
| 68 | 31.60 | 27.10 | 37.30 | 4.0 | 0 | 0 | 230 | 18.0 |
| 69 | 31.80 | 27.40 | 37.80 | 3.0 | 0 | 0 | 140 | 15.0 |
| 70 | 32.10 | 27.60 | 38.30 | 2.0 | 0 | 0 | 180 | 16.5 |
| 71 | 32.40 | 27.80 | 38.80 | 1.0 | 0 | 0 | 320 | 29.0 |
| 72 | 34.00 | 29.00 | 34.00 | 3.0 | 0 | 0 | 97 | 10.3 |
| 73* | 31.01 | 26.58 | 36.39 | 6.02 | 0 | 0 | 125 | 11.0 |
| 74* | 31.01 | 26.08 | 36.39 | 6.02 | 0.5 | 0 | 120 | 8.4 |
| 75* | 31.01 | 25.58 | 36.39 | 6.02 | 1.00 | 0 | 70 | 7.5 |
| 76* | 31.01 | 24.58 | 36.39 | 6.02 | 2.00 | 0 | 97 | 11.5 |
| 77* | 31.01 | 26.58 | 31.39 | 6.02 | 0 | 5.00 | 77 | 8.5 |
| 78* | 31.01 | 24.38 | 31.39 | 6.02 | 2.20 | 5.00 | 62 | 6.8 |
| 79* | 33.51 | 26.58 | 33.89 | 6.02 | 0 | 0 | 85 | 8.1 |
| 80* | 26.01 | 31.58 | 36.39 | 6.02 | 0 | 0 | 132 | 9.8 |
| 81* | 33.51 | 24.08 | 36.39 | 6.02 | 0 | 0 | 125 | 10.0 |
| 82* | 33.00 | 28.00 | 33.00 | 6.00 | 0 | 0 | 62 | 7.5 |
| 83* | 29.53 | 23.22 | 34.66 | 5.73 | 2.10 | 4.76 | 110 | 10.4 |

Table IV shows formulations 67–83 according to the invention, formulations 67, 68, 73–83 lying within the preferred 4% to 7% range of fluorine. In this Table compositions are shown as weight percent of oxides.

To produce the powdered glasses, 800g batches of the compositions shown in Table IV were mixed. The batches were heated in platinum pots in an electric furnace at a temperature of 1500° C. until they melted and then stirred; the glasses formed were then annealed, broken up and powdered.

TABLE V

| | Composition (parts by weight) | | | | | | | Gel Time | Set Time |
|---|---|---|---|---|---|---|---|---|---|
| No. | SiO$_2$ | Al$_2$O$_3$ | CaO$^{(1)}$ | CaF$_2$ | AlF$_3$ | Na$_2$O | B$_2$O$_3$ | (s) | (m) |
| 84* | 33.3 | 37.2 | 19.1 | 13.4 | 0 | 0 | 0 | 144 | 13.9 |
| 85* | 26.7 | 37.4 | 23.2 | 12.7 | 0 | 0 | 0 | 114 | 12.2 |
| 86* | 29.3 | 37.4 | 20.7 | 12.7 | 0 | 0 | 0 | 144 | 13.6 |
| 87* | 32.5 | 32.5 | 22.7 | 12.2 | 0 | 0 | 0 | 96 | 8.8 |
| 88* | 31.8 | 31.8 | 27.3 | 0 | 9.1 | 0 | 0 | 102 | 9.5 |
| 89* | 32.0 | 33.1 | 27.5 | 0 | 7.5 | 0 | 0 | 138 | 11.5 |
| 90* | 31.8 | 37.3 | 17.7 | 12.7 | 0 | 0.5$^{(2)}$ | 0 | 114 | 10.1 |
| 91* | 31.8 | 37.3 | 17.2 | 12.7 | 0 | 1.0$^{(2)}$ | 0 | 96 | 11.8 |
| 92* | 31.8 | 32.2 | 18.2 | 12.7 | 0 | 0 | 5.1$^{(3)}$ | 120 | 12.2 |
| 93* | 31.8 | 32.2 | 15.9 | 12.7 | 0 | 2.3$^{(4)}$ | 5.1$^{(4)}$ | 102 | 11.4 |
| 94* | 30.1 | 35.5 | 15.1 | 12.1 | 0 | 2.2$^{(4)}$ | 4.9$^{(4)}$ | 108 | 12.1 |

Table V shows formulations 84–94 all of which lie within the preferred 5–7% fluorine charged range (4%–6% fluorine in glass) according to the invention. In this Table the glass/acid ratio is 3:1, not 5:1. The conversion to oxide percentages can be carried out in the general manner indicated above in relation to Table I.

(1) is added as calcium carbonate; (2) as sodium carbonate; (3) as boric acid; and (4) as borax.

TABLE VI

| No. | Poly Acid Ref. | Glass to Polyacid Ratio | Water to Powder Ratio | % Tartaric Acid | Gel Time (sec) | Set Time (min) |
|---|---|---|---|---|---|---|
| 66A | ACMB1 | 2½:1 | 0.67 | 11 | 145 | 14.2 |
| B | ACMB1 | 2½:1 | 0.50 | 11 | 132 | 11.8 |
| C | ACMB1 | 2½:1 | 0.40 | 11 | 107 | 12.5 |
| D | ACMB1 | 3:1 | 0.67 | 11 | 122 | 10.5 |
| E | ACMB1 | 3:1 | 0.50 | 11 | 100 | 8.9 |
| F | ACMB1 | 3:1 | 0.40 | 11 | 102 | 9.1 |
| G | ACMB1 | 3½:1 | 0.67 | 11 | 112 | 10.1 |
| H | ACMB1 | 3½:1 | 0.50 | 11 | 90 | 9.1 |
| I | ACMB1 | 3½:1 | 0.40 | 11 | 97 | 9.3 |
| J | ACMB1 | 2½:1 | 0.50 | 0 | 116 | 11.3 |
| K | ACMB1 | 2½:1 | 0.50 | 5 | 85 | 9.0 |
| L | ACMB1 | 2½:1 | 0.50 | 10 | 106 | 10.5 |
| M | ACMB1 | 2½:1 | 0.50 | 15 | 112 | 14.4 |
| N | ACMB1 | 2½:1 | 0.50 | 20 | 175 | 17.6 |
| O | ACMB1 | 2½:1 | 0.50 | 25 | 200 | 15.9 |
| P | ACMB1 | 3:1 | 0.50 | 0 | 145 | 10.9 |
| Q | ACMB1 | 3:1 | 0.50 | 5 | 72 | 9.1 |
| R | ACMB1 | 3:1 | 0.50 | 10 | 100 | 9.3 |
| S | ACMB1 | 3:1 | 0.50 | 15 | 190 | 15.9 |
| T | ACMB1 | 3:1 | 0.50 | 20 | 212 | 16.9 |
| U | ACMB1 | 3:1 | 0.50 | 25 | 240 | 18.3 |
| V | ACMB1 | 3½:1 | 0.50 | 0 | 125 | 12.0 |
| W | ACMB1 | 3½:1 | 0.50 | 5 | 87 | 10.3 |
| X | ACMB1 | 3½:1 | 0.50 | 10 | 102 | 9.2 |
| Y | ACMB1 | 3½:1 | 0.50 | 15 | 130 | 10.7 |
| Z | ACMB1 | 3½:1 | 0.50 | 20 | 188 | 12.0 |

TABLE VI-continued

| No. | Poly Acid Ref. | Glass to Polyacid Ratio | Water to Powder Ratio | % Tartaric Acid | Gel Time (sec) | Set Time (min) |
|---|---|---|---|---|---|---|
| AA | ACMB1 | 3½:1 | 0.50 | 25 | 220 | 14.4 |

Table VI shows the effect of keeping the glass composition the same but altering other variables, specifically the glass: acid ratio, powder:water ratio and percentage of tartaric acid. The glass composition is No. 66 from Table III i.e. a preferred composition according to the invention. The grade of acid, ACMB-1, was equivalent to PAA-1 described above.

TABLE VII

| No. | Poly Acid Ref. | Glass to Polyacid Ratio | Water to Powder Ratio | % Tartaric Acid | Mean Gel Time (sec) | Mean Set Time (min) |
|---|---|---|---|---|---|---|
| 61A | ACMB1 | 3:1 | 0.67 | 11 | 88 | 9.4 |
| B | ACMB1 | 3:1 | 0.50 | 11 | 80 | 9.8 |
| C | ACMB1 | 3:1 | 0.33 | 11 | 93 | 11.2 |
| D | ACMB1 | 5:1 | 0.67 | 11 | 77 | 9.0 |
| E | ACMB1 | 5:1 | 0.50 | 11 | 70 | 8.2 |
| F | ACMB1 | 5:1 | 0.33 | 11 | 48 | 6.8 |
| G | ACMB1 | 3:1 | 0.5 | 0 | 67 | 7.1 |
| H | ACMB1 | 3:1 | 0.5 | 5 | 57 | 6.9 |
| I | ACMB1 | 3:1 | 0.5 | 10 | 80 | 7.6 |
| J | ACMB1 | 3:1 | 0.5 | 15 | 110 | 9.8 |
| K | ACMB1 | 3:1 | 0.5 | 20 | 143 | 12.1 |
| L | ACMB1 | 3:1 | 0.5 | 25 | 138 | 16.0 |
| M | ACMB1 | 5:1 | 0.5 | 0 | 74 | 7.7 |
| N | ACMB1 | 5:1 | 0.5 | 5 | 57 | 7.3 |
| O | ACMB1 | 5:1 | 0.5 | 10 | 53 | 6.8 |
| P | ACMB1 | 5:1 | 0.5 | 15 | 87 | 8.3 |
| Q | ACMB1 | 5:1 | 0.5 | 20 | 118 | 8.8 |
| R | ACMB1 | 5:1 | 0.5 | 25 | 103 | 8.3 |
| S | E7 | 3:1 | 0.5 | 11 | 88 | 8.2 |
| T | E9 | 3:1 | 0.5 | 11 | 40 | 5.2 |

Table VII is broadly equivalent to Table VI but shows variations of formulation No. 61, which is a formulation within the invention but not within the preferred range. E7 and E9 are polyacrylic acids of intrinsic viscosities 0.28 and 0.45 respectively.

TABLE VIII

| No. | Particle Size (microns) | Gel (secs) | Set (mins) |
|---|---|---|---|
| 61U | less than 45 | 55 | 7.2 |
| 61V | 46–53 | 71 | 7.7 |
| 61W | 54–75 | 80 | 9.0 |
| 61X | 76–106 | 119 | 11.7 |

Table VIII again relates to formulation No. 61, used in the conditions of Table I (5:1 glass:acid, 2:1 powder:-water, 11% tartaric acid) but only with narrow particle size ranges of glass powder.

TABLE IX

| No. | Poly-Acid Ref. | Glass Acid Ratio | Water Powder Ratio | % Tartaric Acid | Mean Gel Time (sec) | Mean Set Time (mins) |
|---|---|---|---|---|---|---|
| 14A | ACMB1 | 3:1 | 0.67 | 11 | 102 | 16.4 |
| B | ACMB1 | 3:1 | 0.50 | 11 | 73 | 13.1 |
| C | ACMB1 | 3:1 | 0.33 | 11 | 48 | 10.2 |
| D | ACMB1 | 5:1 | 0.67 | 11 | 52 | 29.0 |
| E | ACMB1 | 5:1 | 0.50 | 11 | 73 | 12.0 |
| F | ACMB1 | 5:1 | 0.33 | 11 | 45 | 8.1 |
| G | ACMB1 | 3:1 | 0.50 | 0 | 65 | 25.0 |
| H | ACMB1 | 3:1 | 0.50 | 5 | 63 | 21.0 |
| I | ACMB1 | 3:1 | 0.50 | 10 | 61 | 21.0 |
| J | ACMB1 | 3:1 | 0.50 | 15 | 78 | 21.5 |
| K | ACMB1 | 3:1 | 0.50 | 20 | 120 | 24.0 |
| L | ACMB1 | 3:1 | 0.50 | 25 | 168 | 27.0 |
| M | ACMB1 | 5:1 | 0.50 | 0 | 67 | 19.3 |
| N | ACMB1 | 5:1 | 0.50 | 5 | 28 | 8.1 |
| O | ACMB1 | 5:1 | 0.50 | 10 | 42 | 8.1 |
| P | ACMB1 | 5:1 | 0.50 | 15 | 60 | 11.2 |
| Q | ACMB1 | 5:1 | 0.50 | 20 | 67 | 15.0 |
| R | ACMB1 | 5:1 | 0.50 | 25 | 87 | 14.5 |
| S | E7 | 3:1 | 0.50 | 11 | 101 | 23.6 |
| T | E9 | 3:1 | 0.50 | 11 | 38 | 24.0 |
| U | E11 | 3:1 | 0.50 | 11 | 25 | 13 |

TABLE IX

Table IX relates to formulation 14 and is thus for comparison only. E 11 is a polyacrylic acid of intrinsic viscosity 0.69.

The information given in the above tables can be laid out in graphical form, and the accompanying drawings show FIGS. 1 to 5 all of which are graphs of gel time in seconds against set time in minutes for the various compositions as shown in the Tables I–IX.

The figures entered on FIG. 1 refer to the formulations listed in Tables I–V, insofar as these can be plotted on the scale provided.

The formulations 1–35 of Table I are entered as bare figures. The zinc oxide formulations 40–52 of Table II, which have two set times are shown as vertical lines of the requisite length joining the two set times. The formulations 60–94 of Tables III–V, according to the invention, are entered as underlined figures, those (66–68, 73–94) within the preferred fluorine range being doubly underlined.

Line OA joins all those points where set time is twelve times as much as gel time; line OB joins those points where set time is six times as much as gel time. (Lines OC and OD join those points where the set:gel time ratios are 4:1 and 8:1 respectively. Box EFGH defines gel times of 90–180 seconds and set times of 5–15 minutes, this being the approximate conventional limits of medical practice. Box JKLM defines the working (110–150 secs) and set (6–10 mins) conditions of the best P.O.P. bandages.

Figure 2:
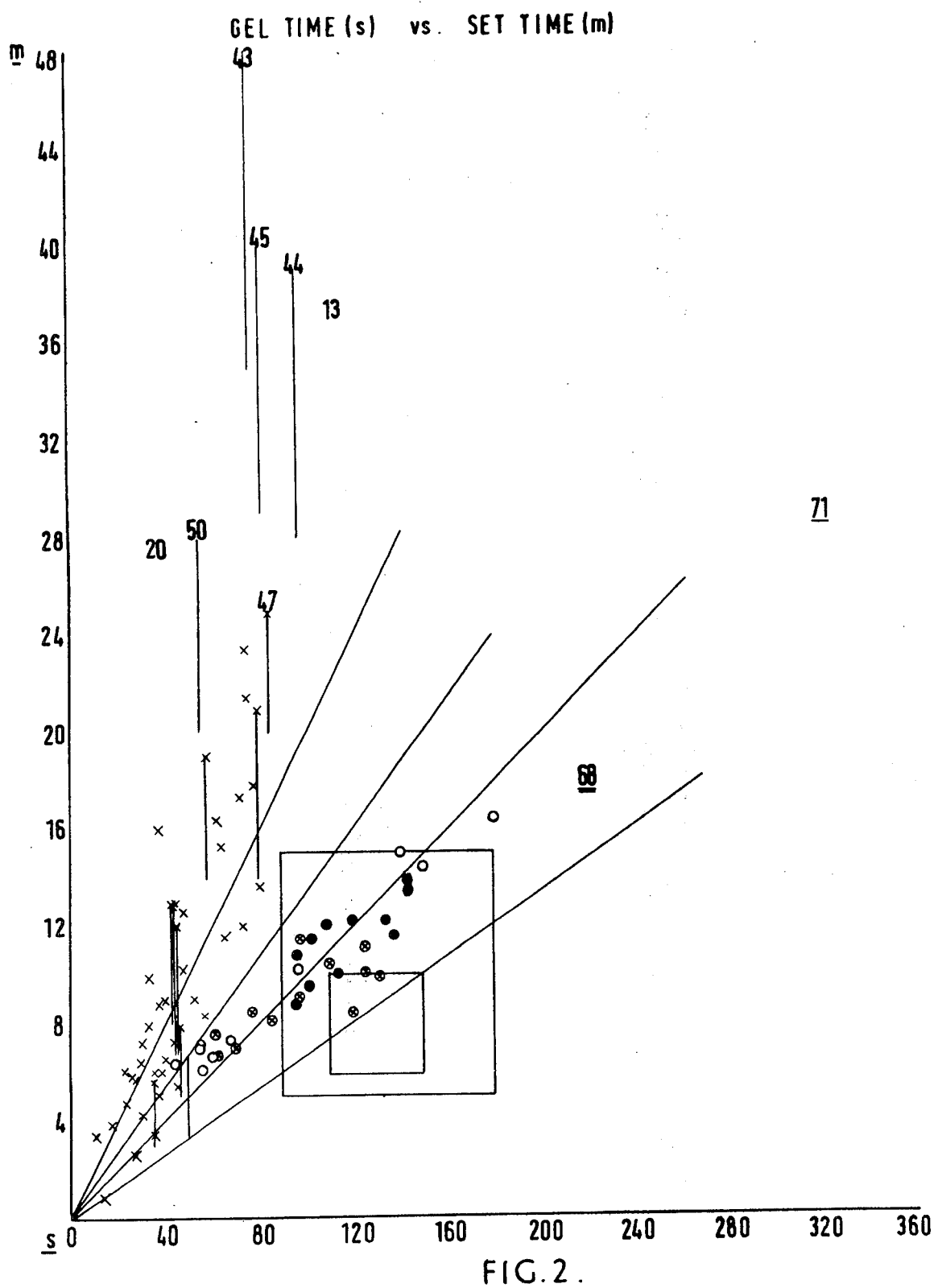

FIG. 2 is generally similar to FIG. 1 but shows larger field on a smaller scale. For clarity, points within the 'FIG. 1' field (as shown on FIG. 2) have not been itemised, but the Tables I and II figures are shown as crosses and the Tables III, IV, V figures as circles, these being crossed for the preferred fluorine range and filled-in for those Table V 3:1 glass:acid ratio formulations. The lines OA, OB, OC, OD and the boxes EFGH and JKLM are shown but not labelled.

Study of FIGS. 1 and 2 shows:

(1) The comparison compositions 1–52 have in general shorter gell times than those of the compositions of the invention.

(2) The comparison compositions have a wider range of set times than those of the present invention.

(3) The set:gel time ratio of the comparison compositions 1–52 is generally 12:1 or more, but that of the compositions of the invention is about 6:1 or less. There are two identifiable trends, best seen in FIG. 2, that of the comparison materials not entering the usual box EFGH of conventional manipulative practice but that of the invention materials falling squarely within it and indeed approaching the best P.O.P. practice shown by the box JKLM.

(4) Lines OC and OD, when cut off by say 50 seconds gel time, indicate that there can be potential military or disaster uses for a lightweight X-ray-transparent waterresistant cast which hardens in 6, 8 or 10 minutes or some such brief period. The comparison compositions, insofar as they provide a rapid-setting material, only allow for a gel time of 20-40 seconds. The present invention however can provide such specialized materials with a usable gel time of about 60 seconds. The disadvantages of using such a gel time (towards the bottom end of usefulness) can be outweighed by the advantage of rapid setting, and lines OC and OD demonstrate this.

(5) As discussed in more detail below, increasing the glass:acid ratio from 3:1 to 5:1 decreases the gel and set times. For true comparison those filled-in circles (formulations 84–94, Table V) should therefore be displaced somewhat towards the origin. This does not affect the trend as shown and indeed gives a tighter population of plotted points for Tables III–V.

Figure 3:
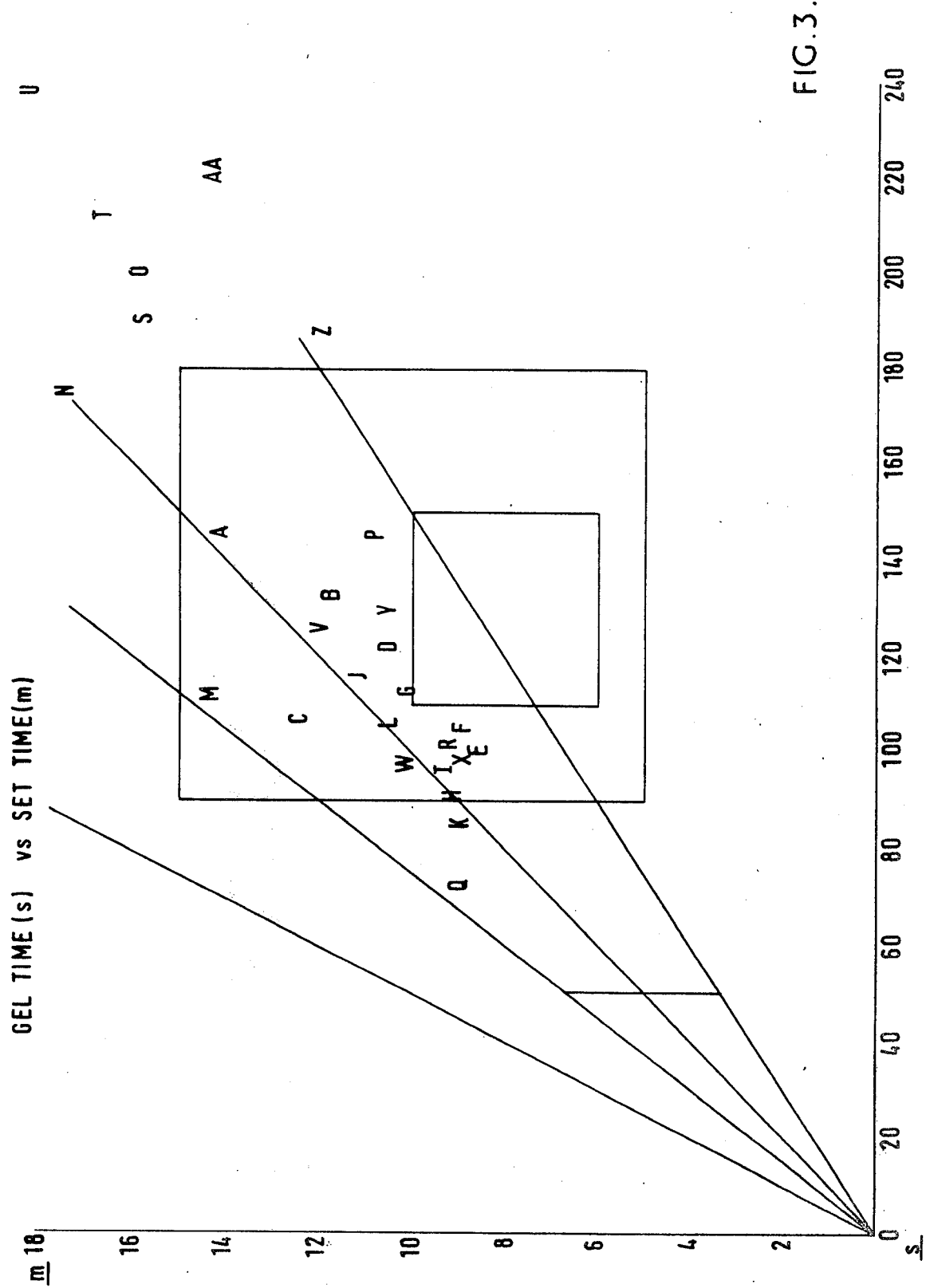
Figure 4:
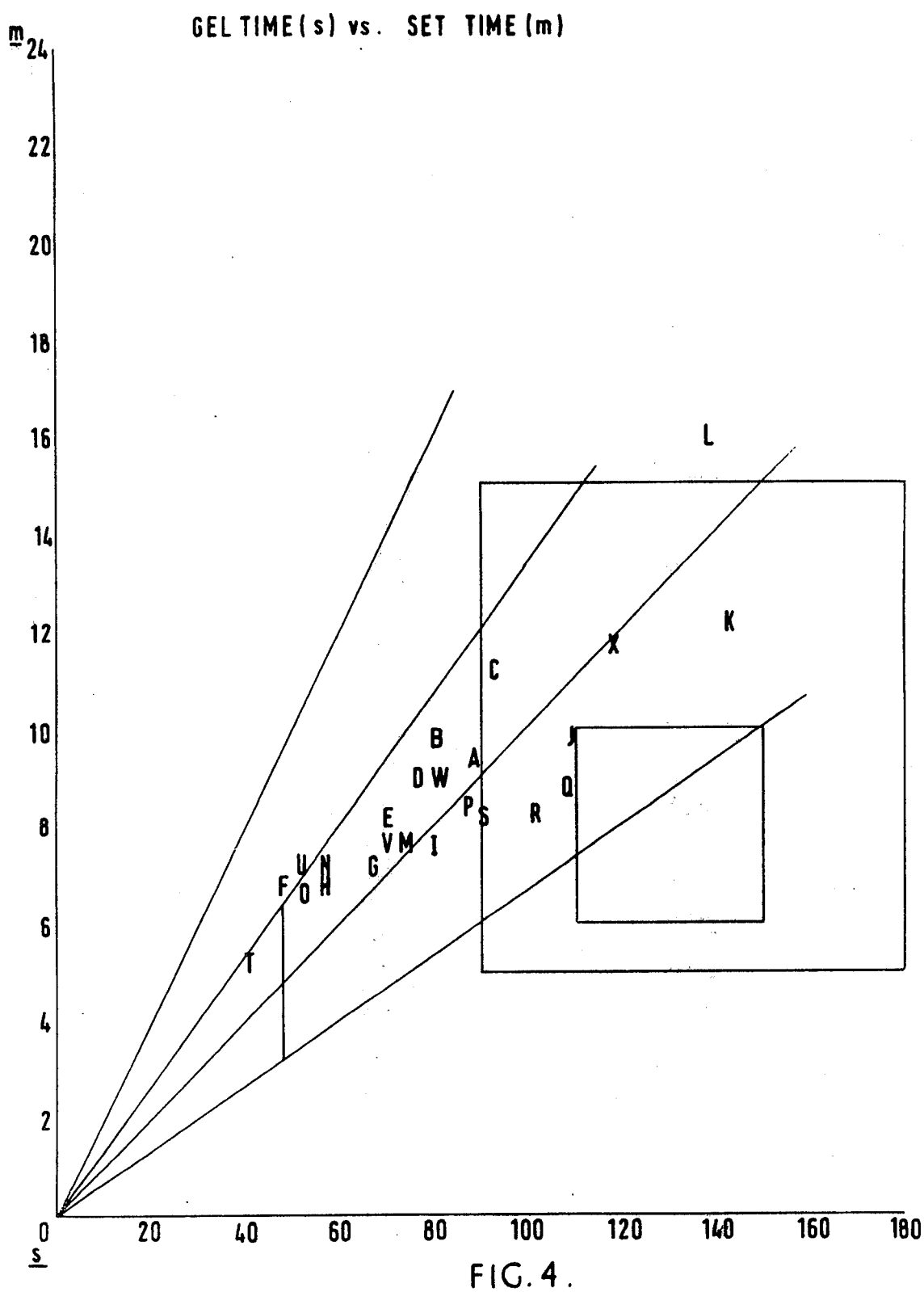
Figure 5:
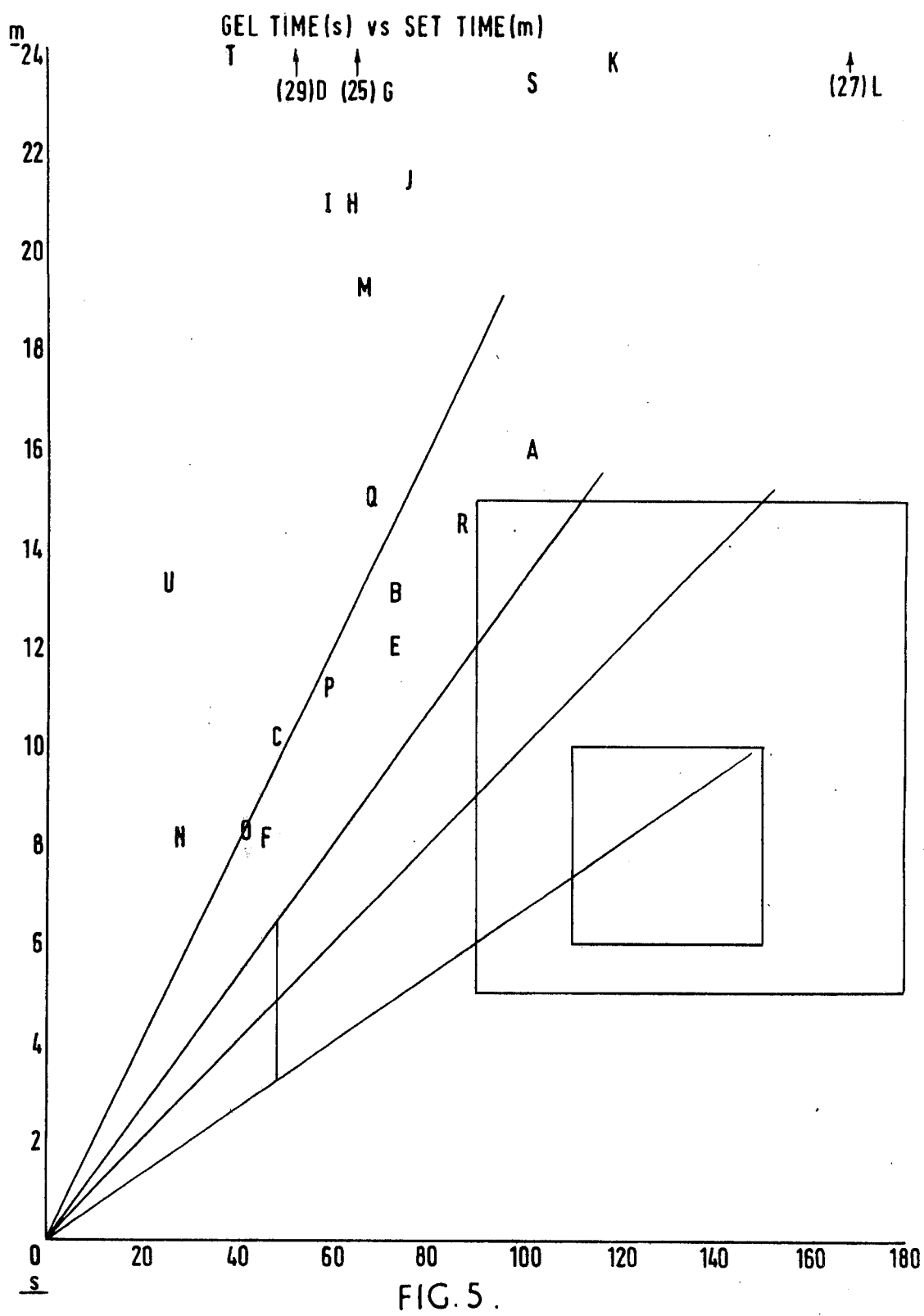

FIGS. 3, 4, 5 show successively, on the same scale as that shown in FIG. 1, the effect on a preferred composition (66) a composition within the invention but outside the preferred range (61) and a comparison composition (14) of varying parameters predominantly such as glass-:polymer ratio, powder:water ratio, and tartaric acid content, but also to a lesser extent such as glass particle size and molecular weight of polymer. As before the various lines of FIG. 1 are drawn in but not labelled.

It will be generally apparent that the gel and set times of compositions 61 and 66, however modified in the above respects, generally stay within, and indeed move farther into, the preferred areas of the graph. Even the borderline composition 61 can be taken comfortably into these acceptable regions. Moreover, they tend to stay around, or even move below, the line defining the 6:1 set:gel ratio. On the other hand the comparison composition 14, when similarly modified, gives gel and set times all outside, and in many cases grossly outside, the desired area, in this instance the points clustering around or exceeding the 12:1 set:gel ratio.

It appears therefore (although the Applicants do not wish or intend to be limited in the scope of their claims by any hypothesis) that the glass composition is a governing factor and that the other variables are subsidiary in nature.

To turn to the Tables VI–IX, and FIGS. 3–5, in more detail:

(1) Glass-to-acid ratio

66 A-D-G, B-E-H, C-F-I
and
61 A-D, B-E, C-F
all show a general decrease of gel and set times as glass:polymer ratio increases.

(2) Water-to-powder ratio

66 A-B-C, D-E-F, G-H-I
and
61 A-B, C-D, E-F
similarly all show a general decrease of gel and set times as water:powder ratio decreases.

(3) Tartaric acid content

66 J to O, 66 P to U, 66 V to AA
61 G to L, 61 M to R

All these show that the gel and set times are initially depressed by addition of tartaric acid but then increase as the percentage of tartaric acid is increased further.

(4) Particle size of glass

61 U to X indicate that the smaller the glass particles the more active the system and the faster the ge, and set times.

(5) Nature of polyacrylic acid

Comparison of results using polymers ACMB1, E7, E9 and E11 in the table suggests that increasing molecular weight decreases the gel and set times. However, too high a molecular weight increases the viscosity of the cement unduly.

While the above discussion has mostly concerned gel and set times there are other features of these materials which should also be discussed. Those are for instance tensile strength and (especially) rate of strength build up; moisture vapour permeability and allied characteristics; and X-ray transparency. Plaster-of-paris bandages become hard in three stages:

(i) The plaster/water slurry, containing both that water needed for chemical reaction and that needed for workability, becomes unworkable, probably because most of the hydration is complete and the gypsum crystals have mostly deposited. This is referred to above as "working time".

(ii) The material sets solid to provide a "green strength", typically in 5–15 minutes, corresponding to the completion of the chemical processes described under (i). This is referred to herein as the "set time".

(iii) The solid cast becomes harder due to evaporation of excess water. This can take from a few hours to one or two days, and will be referred to as the "hardening time".

The patient can be left after stage (ii), but the strength of the case is low and it is easy to damage the wet matrix until the cast has hardened.

Bandages according to the invention have a "gel time" similar in nature to the "working time" for P.O.P. bandages, followed by a "set time". At this stage, however, they have reached a high proportion of their ultimate strength, and the subsequent hardening time only adds a relatively small proportion to this, being in any case over more quickly.

Generally speaking, compositions as described in Tables III–V reach a tensile strength of about twice the 600 psi of P.O.P and rapidly (usually after setting but in any case in about 5 or 6 hours) appear to be as strong as P.O.P. is after 24 hours. Certain variations can affect tensile strength, e.g. increase in glass:acid, water:powder and tartaric acid all decrease tensile strength, although in the latter case the normal 5–15% level of addition is helpful and the relationship is not linear. Increasing the acid molecular weight also increases tensile strength. Overall, however, since the strength and rate of strength buildup is so much improved over P.O.P there is a great deal of latitude available in the formulations.

Immersion of a one-inch (2.54 cm) diameter cylinder of an air-dried cast material based on formulation 66, in distilled water at 20° C. for one-hour and for 24 hours led in each case to a drop in tensile strength of about 8%, the strength being measured by the axial break load and the average being taken of a number of formulations of a 3:1 glass/acid ratio with and without 5% antishrinkage agents. Comparisons on the same basis with two P.O.P casts showed in one instance a 25–30% loss of strength and in the other a 60–65% loss of strength compared to that of the dry cast. The moisture vapour permeability of the casts of the invention is about the same as that for P.O.P, which gives the possibility of casts which allow the patient to be bathed without detrimentally affecting the cast.

X-ray transparency is far better than that of P.O.P while the thickness of the cast can in any case be less. Zinc oxide/polyacrylate cements are virtually X-ray opaque.

By way of example of amnufacture of a bandage:

Hydroxypropyl cellulose (2%) was dissolved in methylene chloride. Glass powder of composition No. 66 and particle size below 45 microns and polyacrylic acid of particle size below 106 microns was added to a solids content of 50%, the hydroxypropyl cellulose being 4% by weight of the solids; the slurry was placed in an application box with a flexible doctor blade and ridging bar and spread at a loading of 300 g/m² solids on a Leno gauze bandage about 9 meters long and 8 cms wide. This loading was such that the gauze components were individually coated, but most of the interstices were unblocked, to provide good wettability. The bandage was thereafter air-dried.

By way of example of a composition formulated to avoid shrinkage:

Anhydrous cement compositions were prepared by mixing 1 part by weight of apparticulate polyacrylic acid (particle size less than 50 microns, molecular wt. about 200,000); 3 parts by weight of a calcium fluoroaluminosilicate glass prepared by fusing at 1500° C. a mixture of (by weight) 26.7% $SiO_2$ 37.4% $Al_2O_3$ 23.2% CaO (added as $CaCO_3$) and 12.7% $CaF_2$; and 0.1 part by weight particulate tartaric acid together with NaCl in the amounts shown below. Each cement was mixed with two parts by weight of water and allowed to set. After 24 hours linear shrinkage was determined, the results being as follows:

With no NaCl - 10.3% linear shrinkage
With 2.5% NaCl, based on total solids by weight - 6.3% linear shrinkage
With 5.0% NaCl - 3.6% linear shrinkage Splinting bandages made up as described above were tested at zero NaCl and 5% NaCl by dipping into water and wrapping around 5-cm diameter formers. Diametral shrinkage was about 5% and 1% respectively 24 hours after hardening.

We claim:

1. A curable composition comprising a calcium fluoroaluminosilicate glass in particulate form and consisting essentially of from 25 to 35% by weight of silicon calculated as silica, from 30 to 40% by weight of aluminum calculated as alumina, from 20 to 35% by weight calcium, calculated as calcium oxide, and an effective amount up to 9% by weight fluorine; together with a crosslinkable material chosen from the group consisting of poly(carboxylic acids) and polymeric precursors thereof.

2. A curable composition as claimed in claim 1 wherein the polymeric precursor is a poly(carboxylic acid anhydride).

3. A curable composition as claimed in claim 1 wherein the same polymer is a homopolymer of an unsaturated compound chosen from the group consisting of (a) monocarboxylic acid (b) monocarboxylic acid anhydride (c) dicarboxylic acid (d) dicarboxylic acid anhydride; (e) copolymers between at least two of (a) (b) (c) and (d); and (f) copolymers between at least one of (a) (b) (c) and (d) and at least one further ethylenically unsaturated monomer.

4. A curable composition as claimed in claim 3 in which the compound is chosen from acrylic, itaconic, mesaconic, citraconic, and maleic acids or anhydrides.

5. A curable composition as claimed in claim 4 in which the said copolymer is between acrylic acid and acrylamide or acrylonitrile.

6. A curable composition as claimed in claim 4 wherein the said copolymer is between maleic acid and methyl vinyl ether.

7. A curable composition as claimed in claim 4 in which the said copolymer is between one of said anhydrides and an ethylenically unsaturated material chosen from the group consisting of ethylene, propylene, butene and styrene.

8. A curable composition as claimed in claim 7 in which the said copolymer is between maleic anhydride and ethylene.

9. A curable composition as claimed in claim 1 in which the polymer molecular weight is from 1,000 to 1,000,000.

10. A curable composition as claimed in claim 9 in which the said molecular weight is from 50,000 to 500,000.

11. A curable composition as claimed in claim 1 formulated as a two-part package of (a) the said particulate glass and (b) the said crosslinkable material.

12. A curable composition as claimed in claim 11 in which the crosslinkable polymeric material is a polyacid in aqueous solution.

13. A curable composition as claimed in claim 1 in the form of a mixture of the particulate glass and solid particulate crosslinkable polymeric material.

14. A curable composition as claimed in claim 13 in which the glass:polymer weight ratio is from 0.5:1 to 5:1.

15. A curable composition as claimed in claim 14 wherein the said ratio is from 1.5:1 to 4.5:1.

16. A curable composition as claimed in claim 13 in which the acid has a particle size below 100 microns.

17. A curable composition as claimed in claim 13 having a gel time of 60 to 300 seconds.

18. A curable composition as claimed in claim 17 wherein the said gel time is from 90 to 180 seconds.

19. A curable composition as claimed in claim 18 wherein the said gel time is from 110 to 150 seconds.

20. A curable composition as claimed in claim 13 having a set time of up to 20 minutes.

21. A curable composition as claimed in claim 20 having a set time of 5 to 15 minutes.

22. A curable composition as claimed in claim 13 wherein the ratio of set time to gel time is from 4:1 to 8:1 and minimum gel time is 60 seconds.

23. A curable composition as claimed in claim 13 further comprising an acid chosen from the group consisting of organic polycarboxylic and hydroxycarboxylic acids, in dry particulate form.

24. A curable composition as claimed in claim 23 in which from 5 to 15% by weight of the said acid is present, based on weight of polymeric material.

25. A curable composition as claimed in claim 23 in which the said acid is chosen from the group consisting of tartaric, succinic, oxalic, citric, ascorbic, gluconic and adipic acids.

26. A curable composition as claimed in claim 13 further comprising a particulate filler.

27. A curable composition as claimed in claim 26 wherein the filler is chosen from silica and alumina.

28. A curable composition as claimed in claim 13 further comprising a particulate watersoluble inorganic crystalline material.

29. A curable composition as claimed in claim 28 wherein said material is a salt of a strong acid and a metal chosen from the group consisting of alkali and alkaline earth metals.

30. A curable composition as claimed in claim 29 wherein the said material is a salt of an alkali metal and hydrochloric acid.

31. A curable composition as claimed in claim 30 wherein the salt is sodium chloride.

32. A curable composition as claimed in claim 28 wherein from 2.5 to 10.0% by weight of said inorganic crystalline material is present, based on total glass and polymer content.

33. A curable composition according to claim 1 wherein the calcium fluoroaluminosilicate glass has up to 7% by weight fluorine.

34. A curable composition according to claim 33 wherein the calcium fluoroaluminosilicate glass has between 4 and 7% by weight fluorine.

35. A curable composition according to claim 33 wherein the calcium fluoroaluminosilicate glass has a fluorine content of 4.5 to 6.0 weight percent.

* * * * *

UNITED STATES PATENT AND TRADEMARK OFFICE
CERTIFICATE OF CORRECTION

PATENT NO. : 4,123,416
DATED : October 31, 1978
INVENTOR(S) : Potter et al.

It is certified that error appears in the above-identified patent and that said Letters Patent are hereby corrected as shown below:

Title Page, [73] Assignee, "Esses" should read -- Essex --.

Column 4, line 62, after "invention" insert -- is --.

Column 7, line 45, before "CaO" delete "0".

Column 7, line 47, before "$Al_2O_3$" delete "0".

Column 10, line 37, "ofwhich" should read -- of which --.

Signed and Sealed this

Third Day of April 1979

[SEAL]

Attest:

RUTH C. MASON
Attesting Officer

DONALD W. BANNER
Commissioner of Patents and Trademarks